US012691071B2

(12) United States Patent
Guo et al.

(10) Patent No.: US 12,691,071 B2
(45) Date of Patent: Jul. 28, 2026

(54) LACOSAMIDE PHARMACEUTICAL COMPOSITION AS WELL AS PREPARATION METHOD AND APPLICATIONS THEREOF

(71) Applicant: SHANGHAI YONSUN BIOTECHNOLOGY CO., LTD., Shanghai (CN)

(72) Inventors: Zhen Guo, Shanghai (CN); Zuyou Chen, Shanghai (CN); Lina Chen, Shanghai (CN); Tingting Wang, Shanghai (CN); Shuhuan Ying, Shanghai (CN); Wenfeng Xie, Shanghai (CN)

(73) Assignee: SHANGHAI YONSUN BIOTECHNOLOGY CO., LTD., Shanghai (CN)

( * ) Notice: Subject to any disclaimer, the term of this patent is extended or adjusted under 35 U.S.C. 154(b) by 303 days.

(21) Appl. No.: 18/551,068

(22) PCT Filed: Mar. 16, 2022

(86) PCT No.: PCT/CN2022/081161

§ 371 (c)(1),
(2) Date: Sep. 18, 2023

(87) PCT Pub. No.: WO2022/194198

PCT Pub. Date: Sep. 22, 2022

(65) Prior Publication Data

US 2024/0156736 A1    May 16, 2024

(30) Foreign Application Priority Data

Mar. 17, 2021    (CN) .......................... 202110286177.2

(51) Int. Cl.
| | |
|---|---|
| *A61K 9/20* | (2006.01) |
| *A61K 9/00* | (2006.01) |
| *A61K 31/165* | (2006.01) |

(52) U.S. Cl.
CPC .......... *A61K 9/2027* (2013.01); *A61K 9/0065* (2013.01); *A61K 9/2009* (2013.01); *A61K 9/2018* (2013.01); *A61K 9/2031* (2013.01); *A61K 9/2054* (2013.01); *A61K 31/165* (2013.01)

(58) Field of Classification Search
None
See application file for complete search history.

(56) References Cited

U.S. PATENT DOCUMENTS

| | | |
|---|---|---|
| 2008/0031945 A1 | 2/2008 | Eisenreich et al. |
| 2012/0219631 A1 | 8/2012 | Kulkarni et al. |
| 2013/0251813 A1 | 9/2013 | Cawello et al. |
| 2015/0104507 A1 | 4/2015 | Cawello et al. |

FOREIGN PATENT DOCUMENTS

| | | |
|---|---|---|
| CN | 101330907 A | 12/2008 |
| CN | 102670544 A | 9/2012 |
| CN | 103561727 A | 2/2014 |
| CN | 111818913 A | 10/2020 |
| CN | 111840239 A | 10/2020 |
| EP | 2801351 A1 | 11/2014 |
| WO | 2018062955 A1 | 4/2018 |

OTHER PUBLICATIONS

Ahn, Jae Soon et al.; "Preparation of Lacosamide Sustained-release Tablets and Their Pharmacokinetics in Beagles and Mini-pigs", Bull. Korean Chem. Soc.; vol. 35, No. 2; Dec. 31, 2014; pp. 557-561.

*Primary Examiner* — Aradhana Sasan
(74) *Attorney, Agent, or Firm* — NKL Law; Allen Xue

(57)    ABSTRACT

A lacosamide pharmaceutical composition as well as a preparation method and application thereof are provided. According to the lacosamide pharmaceutical composition, lacosamide or a pharmaceutically acceptable salt thereof can be dissolved out at the same time, wherein the dissolution rate of the lacosamide pharmaceutical composition is not more than 40% within 1 hour, the dissolution rate of the lacosamide pharmaceutical composition is 20-70% within 6 hours, and the dissolution rate of the lacosamide pharmaceutical composition is not less than 65% within 24 hours. The lacosamide pharmaceutical composition has good slow release performance, the tablet size can be rapidly expanded in the in-vitro dissolution process, the expanded lacosamide pharmaceutical composition has good rigidity and elasticity and has a remarkable retention effect in the stomach, and the cumulative release rate within 24 hours can reach 80% or above.

12 Claims, 2 Drawing Sheets

Dissolution curve of 0.1 N hydrochloric acid solution

Dissolution curve of acetate buffer with pH of 4.5

LACOSAMIDE PHARMACEUTICAL COMPOSITION AS WELL AS PREPARATION METHOD AND APPLICATIONS THEREOF

CROSS-REFERENCE TO RELATED APPLICATIONS

The present application is a U.S. national stage entry of PCT International Application No. PCT/CN2022/081161, filed on Mar. 16, 2022, which claims priority to Chinese Patent Application No. 202110286177.2 and entitled "LACOSAMIDE PHARMACEUTICAL COMPOSITION AS WELL AS PREPARATION METHOD AND APPLICATION THEREOF" filed with China National Intellectual Property Administration on Mar. 17, 2021, the content of which is incorporated herein by reference in its entirety.

TECHNICAL FIELD

The present disclosure belongs to the field of pharmaceutical formulations and relates to a lacosamide pharmaceutical composition, a preparation method therefor and use thereof.

BACKGROUND

Lacosamide has the chemical name of (2R)-2-acetamido-N-benzyl-3-methoxypropanamide, the molecular formula of $C_{13}H_{18}N_2O_3$, and the molecular weight of 250.29400. Lacosamide is suitable for treating patients aged four or more with local epilepsy, and can be used as an auxiliary drug for treating patients aged four or more with primary tonic-clonic epilepsy. Lacosamide is a BCS class I drug and has good water solubility. For example, it is easily soluble in methanol or acetone, and is slightly soluble in acetonitrile or ethanol.

Lacosamide is a novel N-methyl-D-aspartate (NMDA) receptor glycine site antagonist, and belongs to a new class of functional amino acids. It is currently accepted that lacosamide can selectively enhance the slow inactivation of voltage-gated sodium channels (VGSCs), but does not affect the fast inactivation of the sodium channels. Meanwhile, lacosamide may exert an anticonvulsant effect via an action pathway of cross-linking with collapsin response mediator protein 2 (CRMP-2), but the mechanism has not yet been fully elucidated.

Lacosamide has good overall anticonvulsant effect and tolerability, but the adverse effect thereof limits the administration dose to a certain extent. When the patients with epilepsy who are severe or have obvious drug resistance are treated, a serious adverse effect may be caused by greatly increasing the administration dose of lacosamide. In addition, for patients with epilepsy or neuralgia, frequent administration for multiple times a day causes inconvenience to life of the patients, and is liable to cause unstable plasma concentration and induce an adverse effect. Moreover, the lacosamide drug substance has extremely poor flowability and small bulk density. The problems of poor mixing uniformity, overlarge tablet filling depth, difficult unloading and the like exist in the direct tableting of the powder.

Therefore, there is an urgent need to develop a lacosamide pharmaceutical formulation that has low administration frequency, is capable of improving the compliance of patients with epilepsy, has low toxic and side effects, has a good therapeutic effect, and has good plasma concentration stability.

SUMMARY

In order to get improved from the problems described above, the present disclosure provides a lacosamide pharmaceutical composition, wherein the pharmaceutical composition is a 24-hour sustained-release drug. Preferably, under the USP method (dissolution apparatus method 2,900 mL, 0.1N hydrochloric acid, 50 rpm and/or dissolution apparatus method 2,900 mL, an acetate buffer with a pH of 4.5, 50 rpm), the dissolution of the lacosamide pharmaceutical composition simultaneously satisfies the following three characteristics:

A) no more than 40% (preferably no more than 35%, and further preferably no more than 30%) of the active pharmaceutical ingredient is dissolved within 1 hour;

B) 20%-70% (including 20% and 70%, preferably 25%-60%, and further preferably 30%-55%) of the active pharmaceutical ingredient is dissolved within 6 hours;

C) no less than 65% (preferably no less than 70%, and further preferably no less than 80%) of the active pharmaceutical ingredient is dissolved within 24 hours;

wherein the active pharmaceutical ingredient is selected from lacosamide, a pharmaceutically acceptable complex of lacosamide, a pharmaceutically acceptable salt of lacosamide, a pharmaceutically acceptable solvate of lacosamide, and a pharmaceutically acceptable hydrate of lacosamide, preferably lacosamide or a pharmaceutically acceptable salt of lacosamide.

According to an embodiment of the present disclosure, no more than 30% of the active pharmaceutical ingredient of the lacosamide pharmaceutical composition is dissolved within 1 hour, 30%-55% is dissolved within 6 hours, and no less than 80% is dissolved within 24 hours.

The present disclosure also provides a lacosamide pharmaceutical composition, comprising the following components: an active pharmaceutical ingredient, a skeleton material, and a swelling material, wherein the active pharmaceutical ingredient is selected from lacosamide, a pharmaceutically acceptable complex of lacosamide, a pharmaceutically acceptable salt of lacosamide, a pharmaceutically acceptable solvate of lacosamide, and a pharmaceutically acceptable hydrate of lacosamide;

the skeleton material is selected from one or more of a polyvinyl acetate povidone mixture, sodium alginate, and hydroxypropyl methylcellulose;

the swelling material is selected from one or more of polyoxyethylene, carbomer, and sodium alginate.

According to an embodiment of the present disclosure, the lacosamide pharmaceutical composition is a lacosamide gastro-retentive composition, preferably a lacosamide gastro-retentive tablet.

According to an embodiment of the present disclosure, in the lacosamide pharmaceutical composition, the active pharmaceutical ingredient is preferably lacosamide.

According to an embodiment of the present disclosure, the particle size of the active pharmaceutical ingredient is less than or equal to 30 mesh.

According to an embodiment of the present disclosure, the weight percentage of the active pharmaceutical ingredient is preferably 1.0%-50.0%, and further preferably 5.0%-40.0%, such as 20.00% or 18.18%, wherein the weight percentage refers to the percentage of the weight of the active pharmaceutical ingredient to the total weight of the lacosamide pharmaceutical composition.

According to an embodiment of the present disclosure, in the lacosamide pharmaceutical composition, the weight percentage of the swelling material is preferably 1.0%-60.0%, such as 1.0%, 5.0%, 10.0%, 15.0%, 20.0%, 25.0%, 30.0%, 35.0%, 40.0%, 45.0%, 50.0%, 55.0%, or 60.0%, wherein the weight percentage refers to the percentage of the weight of the swelling material to the total weight of the lacosamide pharmaceutical composition.

According to an embodiment of the present disclosure, when the swelling material is polyoxyethylene, the weight percentage of the polyoxyethylene is preferably 5.0%-60.0%, such as 5.0%, 10.0%, 15.0%, 20.0%, 25.0%, 30.0%, 35.0%, 40.0%, 45.0%, 50.0%, 55.0%, or 60.0%, and further preferably 10.0%-40.0%, such as 16.73%, wherein the weight percentage refers to the percentage of the weight of the polyoxyethylene to the total weight of the lacosamide pharmaceutical composition.

According to an embodiment of the present disclosure, when the swelling material is carbomer, the weight percentage of the carbomer is preferably 1.0%-15.0%, and further preferably 1.5%-10%, such as 3.00% or 6.00%, wherein the weight percentage refers to the percentage of the weight of the carbomer to the total weight of the lacosamide pharmaceutical composition.

According to an embodiment of the present disclosure, when the swelling material is sodium alginate, the weight percentage of the sodium alginate is preferably 1.0%-50.0%, such as 1.0%, 5.0%, 10.0%, 15.0%, 20.0%, 25.0%, 30.0%, 35.0%, 40.0%, 45.0%, or 50.0%, and further preferably 1.0%-40.0%, such as 35.09%, 25.45%, or 5.00%, wherein the weight percentage refers to the percentage of the weight of the sodium alginate to the total weight of the lacosamide pharmaceutical composition.

According to an embodiment of the present disclosure, in the lacosamide pharmaceutical composition, the polyvinyl acetate povidone mixture may be a mixture comprising polyvinyl acetate (PVAc) and polyvinylpyrrolidone (PVP), such as a mixture of PVAc and PVP in a weight ratio of 80:19, preferably a mixture comprising PVAc and PVP in 80/19 (w/w) produced by BASF having the trade name of KOLLIDON® SR (abbreviated as "KSR").

According to an embodiment of the present disclosure, the weight percentage of the skeleton material is preferably 1.0%-60.0%, such as 1.0%, 5.0%, 10.0%, 15.0%, 20.0%, 25.0%, 30.0%, 35.0%, 40.0%, 45.0%, 50.0%, 55.0%, or 60.0%, wherein the weight percentage refers to the percentage of the weight of the skeleton material to the total weight of the lacosamide pharmaceutical composition.

According to an embodiment of the present disclosure, when the skeleton material is KSR, the weight percentage of the KSR is preferably 5.0%-60.0%, and further preferably 20.0%-50.0%, such as 24.68% or 18.36%, wherein the weight percentage refers to the percentage of the weight of the KSR to the total weight of the lacosamide pharmaceutical composition.

According to an embodiment of the present disclosure, when the skeleton material is hydroxypropyl methylcellulose, the weight percentage of the hydroxypropyl methylcellulose is preferably 1.0%-30.0%, and further preferably 2.0%-20.0%, such as 17.27%, 8.00%, 16.73%, or 9.09%, wherein the weight percentage refers to the percentage of the weight of the hydroxypropyl methylcellulose to the total weight of the lacosamide pharmaceutical composition.

According to an embodiment of the present disclosure, when the skeleton material is sodium alginate, the weight percentage of the sodium alginate is preferably 1.0%-50.0%, and further preferably 1.0%-40.0%, such as 35.09%, 25.45%, or 5.00%, wherein the weight percentage refers to the percentage of the weight of the sodium alginate to the total weight of the lacosamide pharmaceutical composition.

According to an embodiment of the present disclosure, the skeleton material (such as sodium alginate) can be further used together with a skeleton strength regulator.

According to an embodiment of the present disclosure, the skeleton strength regulator may be selected from water-soluble calcium salts, thereby forming an insoluble calcium alginate gel skeleton with sodium alginate.

According to an embodiment of the present disclosure, the water-soluble calcium salt may be selected from dicalcium phosphate and/or dicalcium phosphate dihydrate, and the like.

According to an embodiment of the present disclosure, the weight percentage of the skeleton regulator is preferably 0%-30.0%, such as 0%, 1.0%, 5.0%, 10.0%, 15.0%, 20.0%, 25.0%, or 30.0%, and further preferably 0%-15.0%, such as 11.73% or 10.91%, wherein the weight percentage refers to the percentage of the weight of the skeleton strength regulator to the total weight of the lacosamide pharmaceutical composition.

According to an embodiment of the present disclosure, the lacosamide pharmaceutical composition described herein may further comprise one or more selected from a disintegrant, a diluent, and a lubricant.

According to an embodiment of the present disclosure, the disintegrant may be selected from, for example, one or more of crospovidone, sodium carboxymethyl starch, croscarmellose sodium, carboxymethylcellulose calcium, low-substituted hydroxypropylcellulose, and the like.

According to an embodiment of the present disclosure, the weight percentage of the disintegrant is preferably 0%-30.0%, such as 0%, 1.0%, 5.0%, 10.0%, 15.0%, 20.0%, 25.0%, or 30.0%, and further preferably 5%-30.0%, such as 20.00%, 16.64%, 13.64%, or 16.36%, wherein the weight percentage refers to the percentage of the weight of the disintegrant to the total weight of the lacosamide pharmaceutical composition.

According to an embodiment of the present disclosure, in the lacosamide pharmaceutical composition, the diluent is preferably selected from one or more of dextrose, lactose monohydrate, anhydrous lactose, sucrose, mannitol, xylitol, sorbitol, microcrystalline cellulose, starch, pregelatinized starch, dicalcium phosphate dihydrate, anhydrous dicalcium phosphate, and cyclodextrin or a derivative thereof.

According to an embodiment of the present disclosure, the weight percentage of the diluent is preferably 0-40%, such as 0%, 1.0%, 5.0%, 10.0%, 15.0%, 20.0%, 25.0%, 30.0%, 30.5%, or 40.0%, such as 20.00% or 15.00%, wherein the weight percentage refers to the percentage of the weight of the diluent to the total weight of the lacosamide pharmaceutical composition.

According to an embodiment of the present disclosure, in the lacosamide pharmaceutical composition, the lubricant is a substance that facilitates the processing steps of mixing, granulating, tableting, and the like of the components, and may be selected from one or more of talc, stearic acid, metal stearates, stearates, colloidal silica, glyceryl behenate, sodium lauryl sulfate, hydrogenated vegetable oil, mineral oil, poloxamer, polyethylene glycol, and sodium chloride.

According to an embodiment of the present disclosure, the metal stearate may be magnesium stearate; the stearate may be glyceryl stearate.

According to an embodiment of the present disclosure, the weight percentage of the lubricant is preferably 0-3.0%, such as 0%, 0.5%, 1.0%, 1.5%, 2.0%, 2.5%, or 3.0%, and further preferably 0.5%-2.0%, such as 1.10%, 1.20%, or 1.65%, wherein the weight percentage refers to the percentage of the total weight of the lubricant to the total weight of the lacosamide pharmaceutical composition.

According to an embodiment of the present disclosure, the lacosamide pharmaceutical composition preferably comprises the following components: an active pharmaceutical ingredient, a skeleton material, a skeleton strength regulator (optionally present), a swelling material, a disintegrant, and a lubricant, or consists of the components described above, wherein the active pharmaceutical ingredient is selected from lacosamide, a pharmaceutically acceptable complex of lacosamide, a pharmaceutically acceptable salt of lacosamide, a pharmaceutically acceptable solvate of lacosamide, and a pharmaceutically acceptable hydrate of lacosamide;

the skeleton material is selected from one or more of a polyvinyl acetate povidone mixture (such as KSR), sodium alginate, and hydroxypropyl methylcellulose;

the swelling material is polyoxyethylene and/or carbomer and/or sodium alginate.

According to an embodiment of the present disclosure, the lacosamide pharmaceutical composition further preferably comprises the following component one, component two, component three, component four, component five, or component six, or consists of the following component respectively:

component one: lacosamide, sodium alginate, crospovidone, anhydrous dicalcium phosphate, magnesium stearate, carbomer, and hydroxypropyl methylcellulose;

component two: lacosamide, polyvinyl acetate povidone mixture, crospovidone, magnesium stearate, sorbitol, carbomer, and hydroxypropyl methylcellulose;

component three: lacosamide, sodium alginate, crospovidone, hydroxypropyl methylcellulose, colloidal silica, magnesium stearate, and anhydrous dicalcium phosphate;

component four: lacosamide, sodium alginate, crospovidone, polyoxyethylene, colloidal silica, magnesium stearate, and anhydrous dicalcium phosphate;

component five: lacosamide, sodium alginate, crospovidone, colloidal silica, magnesium stearate, hydroxypropyl methylcellulose, polyvinyl acetate povidone mixture, and dicalcium phosphate dihydrate;

component six: lacosamide, polyvinyl acetate povidone mixture, crospovidone, magnesium stearate, sorbitol, sodium alginate, carbomer, and hydroxypropyl methylcellulose.

According to an exemplary embodiment of the present disclosure, the lacosamide pharmaceutical composition is further preferably any one of the following formulas:

formula one: 18.18% lacosamide, 35.09% sodium alginate, 13.64% crospovidone (Kollidon CL, BASF), 11.73% anhydrous dicalcium phosphate, 1.10% magnesium stearate, 3.00% carbomer (971 PNF, Lubrizol), and 17.27% hydroxypropyl methylcellulose (K 4M, Ashland);

formula two: 20.00% lacosamide, 24.80% polyvinyl acetate povidone mixture, 20.00% crospovidone (Kollidon CL, BASF), 1.20% magnesium stearate, 20.00% sorbitol, 6.00% carbomer (971 PNF, Lubrizol), and 8.00% hydroxypropyl methylcellulose (K 4M, Ashland);

formula three: 18.18% lacosamide, 35.09% sodium alginate, 16.64% crospovidone (Kollidon CL, BASF), 16.73% hydroxypropyl methylcellulose (K 15M, Ashland), 0.55% colloidal silica, 1.10% magnesium stearate, and 11.73% anhydrous dicalcium phosphate;

formula four: 18.18% lacosamide, 35.09% sodium alginate, 16.64% crospovidone (Kollidon CL, BASF), 16.73% polyoxyethylene (WSR COAGULANT, DowDuPont), 0.55% colloidal silica, 1.10% magnesium stearate, and 11.73% anhydrous dicalcium phosphate;

formula five: 18.18% lacosamide, 25.45% sodium alginate, 16.36% crospovidone (Kollidon CL, BASF), 0.55% colloidal silica, 1.10% magnesium stearate, 9.09% hydroxypropyl methylcellulose (K 15M, Ashland), 18.36% polyvinyl acetate povidone mixture, and 10.91% dicalcium phosphate dihydrate;

formula six: 20.00% lacosamide, 24.80% polyvinyl acetate povidone mixture, 20.00% crospovidone (Kollidon CL, BASF), 1.20% magnesium stearate, 15.00% sorbitol, 5.00% sodium alginate, 6.00% carbomer (971 PNF, Lubrizol), and 8.00% hydroxypropyl methylcellulose (K 4M, Ashland).

Preferably, the lacosamide pharmaceutical composition described above is a 24-hour sustained-release drug. Preferably, under the USP method (dissolution apparatus method 2,900 mL, 0.1N hydrochloric acid, 50 rpm and/or dissolution apparatus method 2,900 mL, an acetate buffer with a pH of 4.5, 50 rpm), the dissolution of the lacosamide pharmaceutical composition simultaneously satisfies the following three characteristics:

A) no more than 40% (preferably no more than 35%, and further preferably no more than 30%) of the active pharmaceutical ingredient, e.g., lacosamide or a pharmaceutically acceptable salt thereof, is dissolved within 1 hour;

B) 20%-70% (preferably 25%-60%, and further preferably 30%-55%) of the active pharmaceutical ingredient, e.g., lacosamide or a pharmaceutically acceptable salt thereof, is dissolved within 6 hours, including 20% and 70%;

C) no less than 65% (preferably no less than 70%, and further preferably no less than 80%) of the active pharmaceutical ingredient, e.g., lacosamide or a pharmaceutically acceptable salt thereof, is dissolved within 24 hours.

For example, no more than 30% of the lacosamide pharmaceutical composition described above is dissolved within 1 hour, 30%-55% is dissolved within 6 hours, and no less than 80% is dissolved within 24 hours.

The present disclosure also provides a preparation method for the lacosamide pharmaceutical composition, and the preparation method comprises a dry granulation process.

According to an exemplary embodiment of the present disclosure, the dry granulation process comprises the following steps:

step 1: sieving the active pharmaceutical ingredient (also called "lacosamide drug substance") to remove lumps to give the sieved lacosamide drug substance;

step 2: mixing the sieved lacosamide drug substance obtained in step 1 with part of the skeleton material, the optionally present skeleton strength regulator, and the disintegrant to give a premix;

step 3: drying and sizing the premix obtained in step 2 via a granulator, then adding an internal lubricant (such as magnesium stearate), mixing, and performing dry granulation to give a granule;

step 4: mixing the rest skeleton material, the swelling material, and a filler with the granule obtained in step 3, then adding an external lubricant (such as magnesium stearate), successively mixing for a period of time, and tableting to give the lacosamide pharmaceutical composition, such as a lacosamide gastro-retentive tablet;

or, according to an exemplary embodiment of the present disclosure, the dry granulation process comprises the following steps:

step 1: sieving a lacosamide drug substance to remove lumps to give the sieved lacosamide drug sub stance;

step 2: mixing the sieved lacosamide drug substance obtained in step 1 with the skeleton material, the swelling material, the disintegrant, and the lubricant (such as colloidal silica) to give a premix;

step 3: drying and sizing the premix obtained in step 2 via a granulator, then adding an internal lubricant (such as magnesium stearate), mixing, and performing dry granulation to give a granule;

step 4: mixing the skeleton strength regulator with the granule obtained in step 3, then adding an external lubricant (such as magnesium stearate), successively mixing for a period of time, and tableting to give the lacosamide pharmaceutical composition, such as a lacosamide gastro-retentive tablet;

or, according to an exemplary embodiment of the present disclosure, the dry granulation process comprises the following steps:

step 1: sieving a lacosamide drug substance to remove lumps to give the sieved lacosamide drug sub stance;

step 2: mixing the sieved lacosamide drug substance obtained in step 1 with the swelling material, the disintegrant, and the lubricant (such as colloidal silica) to give a premix;

step 3: drying and sizing the premix obtained in step 2 via a granulator, then adding an internal lubricant (such as magnesium stearate), mixing, and performing dry granulation to give a granule; step 4: mixing the skeleton strength regulator and the skeleton material with the granule obtained in step 3, then adding an external lubricant (such as magnesium stearate), successively mixing for a period of time, and tableting to give the lacosamide pharmaceutical composition, such as a lacosamide gastro-retentive tablet;

or, according to an exemplary embodiment of the present disclosure, the dry granulation process comprises the following steps:

step 1: sieving a lacosamide drug substance to remove lumps to give the sieved lacosamide drug sub stance;

step 2: mixing the sieved lacosamide drug substance obtained in step 1 with the swelling material, the disintegrant, and the lubricant (such as colloidal silica) to give a premix;

step 3: drying and sizing the premix obtained in step 2 via a granulator, successively mixing for a period of time, then adding an internal lubricant (such as magnesium stearate), mixing, and performing dry granulation to give a granule;

step 4: mixing the skeleton strength regulator and the skeleton material with the granule obtained in step 3, then adding an external lubricant (such as magnesium stearate), successively mixing for a period of time, and tableting to give the lacosamide pharmaceutical composition, such as a lacosamide gastro-retentive tablet.

The present disclosure also provides use of the lacosamide pharmaceutical composition for the manufacturing of a medicament, preferably a medicament for the treatment and/or prevention of acute and chronic pain.

According to an embodiment of the present disclosure, the "acute and chronic pain" is particularly non-neuropathic inflammatory pain, including chronic inflammatory pain, such as rheumatoid arthritis pain and/or secondary osteoarthritis pain.

According to an embodiment of the present disclosure, the "chronic pain" is pain which extends over a period of time, for example, 3-6 months or more, but before or after the period of time, the following characteristic signs are present, and vegetative nervous dysfunction signs may occur, such as lassitude, sleep disorders, decreased appetite, loss of taste, weight loss, hyposexuality, and/or constipation.

The present disclosure also provides a method for treating and/or preventing acute and chronic pain, and the method comprises orally administering the lacosamide pharmaceutical composition or the lacosamide gastro-retentive tablet described above to a patient once daily.

The present disclosure also provides a lacosamide gastro-retentive tablet, which comprises the lacosamide pharmaceutical composition. Preferably, the specification of the lacosamide gastro-retentive tablet may be selected from 100 mg to 400 mg, such as 100 mg, 200 mg, or 400 mg.

According to an embodiment of the present disclosure, when the lacosamide pharmaceutical composition or the lacosamide gastro-retentive tablet is taken integrally and enters the stomach of a patient, the lacosamide pharmaceutical composition or the lacosamide gastro-retentive tablet can be rapidly expanded or swelled in gastric juice, and has good rigidity and elasticity after expansion, thereby having a significant gastro-retentive effect.

In the context of the present disclosure, the "pharmaceutically acceptable" refers to those substances which are, within the scope of sound medical judgment, suitable for use in contact with the tissues of patients without undue toxicity, irritation, allergic response and the like, commensurate with a reasonable benefit to risk ratio, and effective for their intended use.

In the context of the present disclosure, the "solvate" refers to a molecular complex comprising a drug (e.g., lacosamide) and a stoichiometric or non-stoichiometric amount of one or more pharmaceutically acceptable solvent molecules (e.g., ethanol). When the solvent is closely associated with the drug, the complex formed has a well-defined stoichiometry independent of humidity. However, when the solvent is weakly associated (as in channel solvates and hygroscopic compounds), the solvent content depends on humidity and drying conditions. In this case, the complex is generally non-stoichiometric.

In the context of the present disclosure, the "hydrate" refers to a solvate comprising a drug and a stoichiometric or non-stoichiometric amount of water.

In the context of the present disclosure, the polyvinylpolypyrrolidone (PVPP) is also known as crospovidone or crospovidonum, which is a water-insoluble synthetic cross-linked homopolymer of N-ethenyl-2-pyrrolidone. The exact molecular weight has not yet been determined due to the water insolubility of the material itself. The crospovidone may be produced by BASF and have the trade name of KOLLIDON, or may be produced by ISP and have the trade name of POLYPLASDONE™ with the supplier being Ashland.

According to an embodiment of the present disclosure, the polyvinyl acetate (PVAc) is a homopolymer of vinyl acetate, typically having a molecular weight (Mw) of about $1\times10^5$ to about $1\times10^6$.

According to an embodiment of the present disclosure, the polyethylene oxide (PEO) is also known as polyoxirane or polyethylene. Polyethylene oxide is a homopolymer of oxirane, typically having a molecular weight (Mw) of about $1\times10^5$ to about $1\times10^7$ or about $1\times10^6$ to about $1\times10^7$. Polyethylene oxide is available in various grades based on molecular weight, and may be produced by Union Carbide with the trade name of POLYOX®).

The preferred conditions described above may be combined arbitrarily to obtain preferred embodiments of the present disclosure without departing from the general knowledge in the art.

The reagents and starting materials used in the present disclosure are commercially available.

Beneficial Effects

The lacosamide pharmaceutical composition provided by the present disclosure has good sustained-release performance, and the tablet dimension can be rapidly expanded in an in-vitro dissolution process, the lacosamide pharmaceutical composition provided by the present disclosure has good sustained-release performance, and the tablet dimension can be rapidly expanded in an in-vitro dissolution process. Thus, the lacosamide pharmaceutical composition has good rigidity and elasticity after expansion, and has a significant gastro-retentive effect. The lacosamide pharmaceutical composition provided by the present disclosure has stable properties and is suitable for being orally administered once daily. When administered in a solid dosage form, the pharmaceutical composition has a gastro-retentive time of 12 hours or more and a 24-hour cumulative release rate of 80% or more. The pharmaceutical composition can continuously release lacosamide when being retained in stomach. The dissolution test of the lacosamide gastro-retentive tablet provided by the present disclosure is performed in a hydrochloric acid solution with a pH of 1.0 and/or an acetate buffer with a pH of 4.5 with the volume of 900 mL by adopting the second method of USP with the rotation speed of 50 rpm, and the 24-hour cumulative release rate can reach 80% or more.

According to the preparation process of the present disclosure, the problems of difficulty in filling, unstable tablet weight and the like in the tableting process caused by poor flowability and excessively low bulk density of the drug substance are significantly improved. Moreover, the process is stable and the process parameters are adjustable and controllable, which is beneficial to large-scale production of the product. The preparation process has a good market prospect.

DETAILED DESCRIPTION

Figures 1, 2:
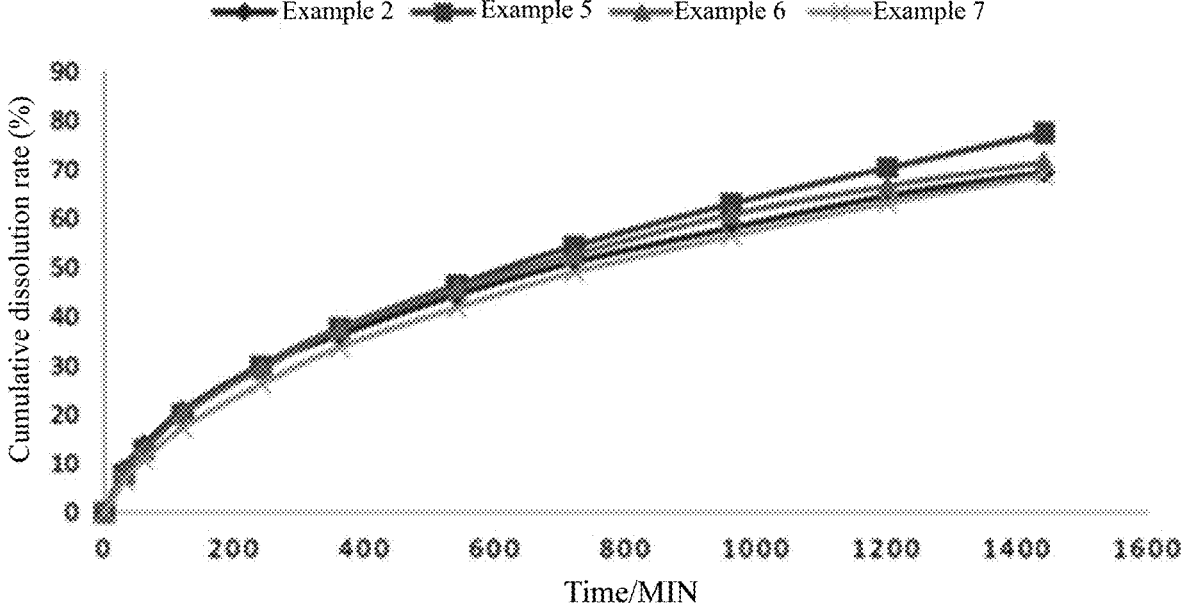
FIG. 1 is a graph of the dissolution curves of the samples in Examples 2, 5, 6, and 7 in 0.1N hydrochloric acid.
FIG. 2 is a graph of the dissolution curves of the samples in Examples 1-7 in an acetate buffer with a pH of 4.5.

The present disclosure is further illustrated by the following examples; however, these examples should not be construed as limiting the present disclosure. Experimental procedures without specified conditions in the following examples are conducted in accordance with conventional procedures and conditions, or in accordance with the manufacturer's manual. In addition, the examples of the present disclosure are compared with the Reference Example, and the significant advantages of the present disclosure in the sustained-release and gastro-retentive effects are further proved.

Reference Example 1

A one-time import commercially available control drug of lacosamide tablets (100 mg, U.S., UCB Pharma SA) was for later use.

Example 1

Matrix tablets containing the following components were produced according to the following procedures, in a batch of about 70 g.

| Component | Weight (mg) | Percentage (%) |
|---|---|---|
| Lacosamide | 200 | 18.18 |
| Sodium alginate | 386 | 35.09 |
| Crospovidone (Kollidon CL, BASF) | 150 | 13.64 |
| Anhydrous dicalcium phosphate | 129 | 11.73 |
| Magnesium stearate (internal) | 6 | 0.55 |
| Carbomer (971 PNF, Lubrizol) (external) | 33 | 3.00 |
| Hydroxypropyl methylcellulose (K 4M, Ashland) (external) | 190 | 17.27 |
| Magnesium stearate (external) | 6 | 0.55 |
| Total | 1100 | / |

Process Steps:

1) A lacosamide drug substance was sieved via a 30-mesh sieve to remove lumps to give the sieved lacosamide drug substance.

2) The sieved lacosamide drug substance obtained in step 1 was taken, and sodium alginate, the lacosamide, crospovidone, and anhydrous dicalcium phosphate were placed into a mixing tank for mixing for about 20 min to give a premix.

3) The premix obtained in step 2 was sized via a granulator with the pore size of the sieve being 2.0 mm and the sizing speed being 200 rpm. Then internal magnesium stearate was added thereto, the mixture was successively mixed for about 5 min, and dry granulation was performed to give a granule. The pinch roller pressure of the dry granulation was about 0-20 kg/cm', the pinch roller rotation speed was 8 HZ, the feeding speed was 3 HZ, the sizing rotation speed was 12 HZ, and the pore size of the selected secondary sizing sieve was 0.8 mm.

4) The amount of the external materials was converted, external hydroxypropyl methylcellulose and carbomer were added, and the mixture was successively mixed for about 15 min. Then external magnesium stearate was added, and the mixture was successively mixed for 5 min. The final mixed material was compressed into a tablet (22.0 mm×10.9 mm almond-shaped shallow-arc stamp die).

The in vitro release of lacosamide was measured using USP (dissolution apparatus method 2,900 mL, an acetate buffer with a pH of 4.5, 50 rpm), and the in vitro release results are as follows:

| Time (min) | Cumulative release rate (%) |
|---|---|
| 0 | 0 |
| 30 | 4.5 |
| 60 | 7.9 |
| 120 | 13.6 |
| 240 | 23.1 |
| 360 | 31.5 |
| 540 | 43.3 |
| 720 | 53.5 |
| 960 | 67.9 |
| 1200 | 83.7 |
| 1440 | 92.5 |

The tablet dimension after dissolution and the results of rigidity and elasticity tests are as follows:

| Tablet dimension (mm × mm × mm) 24 h after dissolution | Rigidity (gf) | Elasticity |
|---|---|---|
| 41.55*21.32*16.64 | 47.2 | 0.429 |

Example 2

Matrix tablets containing the following components were produced according to the following procedures, in a batch of about 160 g.

| Component | Weight (mg) | Percentage (%) |
|---|---|---|
| Lacosamide | 200 | 20.00 |
| Polyvinyl acetate povidone mixture (KSR) | 248 | 24.80 |
| Crospovidone (Kollidon CL, BASF) | 200 | 20.00 |
| Magnesium stearate (internal) | 6 | 0.60 |
| Sorbitol (external) | 200 | 20.00 |
| Carbomer (971 PNF, Lubrizol) (external) | 60 | 6.00 |
| Hydroxypropyl methylcellulose (external) | 80 | 8.00 |
| Magnesium stearate (external) | 6 | 0.60 |
| Total | 1000 | / |

Process Steps:

1) A lacosamide drug substance was sieved via a 30-mesh sieve to remove lumps to give the sieved lacosamide drug substance.

2) The sieved lacosamide drug substance obtained in step 1 was taken, and a polyvinyl acetate povidone mixture, the lacosamide, and crospovidone were placed into a mixing tank for mixing for about 20 min to give a premix.

3) The premix obtained in step 2 was sized via a granulator with the pore size of the sieve being 2.0 mm and the sizing speed being 200 rpm. Then internal magnesium stearate was added thereto, the mixture was successively mixed for about 5 min, and dry granulation was performed to give a granule. The pinch roller pressure of the dry granulation was about 0-20 kg/cm', the pinch roller rotation speed was 8 HZ, the feeding speed was 2 HZ, the sizing rotation speed was 12 HZ, and the pore size of the selected secondary sizing sieve was 0.8 mm.

4) The amount of the external materials was converted, hydroxypropyl methylcellulose, sorbitol, and carbomer were added to the granule obtained in step 3, and the mixture was successively mixed for about 15 min. The amount of external magnesium stearate was converted, the external magnesium stearate was then added, and the mixture was successively mixed for about 5 min. The final mixed material was compressed into a tablet (22.0 mm×10.9 mm almond-shaped shallow-arc stamp die). The in vitro release of lacosamide was measured using USP (dissolution apparatus method 2,900 mL, 0.1N hydrochloric acid and an acetate buffer with a pH of 4.5, 50 rpm), and the in vitro release results are as follows:

| | Cumulative release rate (%) | |
|---|---|---|
| Time (min) Dissolution medium | 0.1N hydrochloric acid | acetate buffer with a pH of 4.5 |
| 0 | 0.0 | 0.0 |
| 30 | 8.8 | 7.4 |
| 60 | 13.8 | 11.9 |
| 120 | 20.8 | 19.0 |
| 240 | 30.1 | 30.1 |
| 360 | 36.4 | 39.1 |
| 540 | 44.5 | 49.8 |
| 720 | 51.1 | 58.6 |
| 960 | 58.1 | 68.4 |
| 1200 | 64.6 | 76.0 |
| 1440 | 69.5 | 82.8 |

The tablet dimension after dissolution and the results of rigidity and elasticity tests are as follows:

| Dissolution medium Tablet dimension (mm × mm × mm) | 0.1N hydrochloric acid | |
|---|---|---|
| 24 h after dissolution | Rigidity (gf) | Elasticity |
| 26.92*13.78*9.96 | 488.8 | 0.800 |

| Dissolution medium Tablet dimension (mm × mm × mm) | acetate buffer with a pH of 4.5 | |
|---|---|---|
| 24 h after dissolution | Rigidity (gf) | Elasticity |
| 32.94*17.29*11.91 | 136.0 | 0.853 |

Example 3

Matrix tablets containing the following components were produced according to the following procedures, in a batch of about 70 g.

| Component | Weight (mg) | Percentage (%) |
|---|---|---|
| Lacosamide | 200 | 18.18 |
| Sodium alginate | 386 | 35.09 |
| Crospovidone (Kollidon CL, BASF) | 183 | 16.64 |
| Hydroxypropyl methylcellulose (K 15M, Ashland) | 184 | 16.73 |
| Colloidal silica | 6 | 0.55 |
| Magnesium stearate (internal) | 6 | 0.55 |
| Anhydrous dicalcium phosphate (external) | 129 | 11.73 |
| Magnesium stearate (external) | 6 | 0.55 |
| Total | 1100 | / |

Process Steps:

1) A lacosamide drug substance was sieved via a 30-mesh sieve to remove lumps to give the sieved lacosamide drug substance.

2) Sodium alginate, the lacosamide drug substance obtained in step 1, crospovidone, hydroxypropyl methylcellulose, and colloidal silica were placed into a mixing tank for mixing for about 20 min to give a premix.

3) The premix obtained in step 2 was sized via a granulator with the pore size of the sieve being 2.0 mm and the sizing speed being 200 rpm. Then internal magnesium stearate was added thereto, the mixture was successively mixed for about 5 min, and dry granulation was performed to give a granule. The pinch roller pressure of the dry granulation was about 0-20 kg/cm', the pinch roller rotation speed was 8 HZ, the feeding speed was 3 HZ, the sizing rotation speed was 12 HZ, and the pore size of the selected secondary sizing sieve was 0.8 mm.

4) The amount of the external materials was converted, external anhydrous dicalcium phosphate was added to the granule obtained in step 3, and the mixture was successively mixed for about 15 min. The amount of external magnesium stearate was converted, the external magnesium stearate was then added, and the mixture was successively mixed for about 5 min. The final mixed material was compressed into a tablet (22.0 mm×10.9 mm almond-shaped shallow-arc stamp die).

The in vitro release of lacosamide was measured using USP (dissolution apparatus method 2,900 mL, an acetate buffer with a pH of 4.5, 50 rpm), and the in vitro release results are as follows:

| Time (min) | Cumulative release rate (%) |
|---|---|
| 0 | 0 |
| 30 | 4.6 |
| 60 | 7.8 |
| 120 | 13.1 |
| 240 | 22.6 |
| 360 | 31.6 |
| 540 | 45.0 |
| 720 | 59.0 |
| 960 | 75.8 |
| 1200 | 86.5 |
| 1440 | 92.5 |

The tablet dimension after dissolution and the results of rigidity and elasticity tests are as follows:

| Tablet dimension (mm × mm × mm) 24 h after dissolution | Rigidity (gf) | Elasticity |
|---|---|---|
| 36.60*22.99*20.50 | 613.2 | 0.621 |

Example 4

Matrix tablets containing the following components were produced according to the following procedures, in a batch of about 70 g.

| Component | Weight (mg) | Percentage (%) |
|---|---|---|
| Lacosamide | 200 | 18.18 |
| Sodium alginate | 386 | 35.09 |
| Crospovidone (Kollidon CL, BASF) | 183 | 16.64 |
| Polyoxyethylene (WSR COAGULANT, DowDuPont) | 184 | 16.73 |

-continued

| Component | Weight (mg) | Percentage (%) |
|---|---|---|
| Colloidal silica | 6 | 0.55 |
| Magnesium stearate (internal) | 6 | 0.55 |
| Anhydrous dicalcium phosphate (external) | 129 | 11.73 |
| Magnesium stearate (external) | 6 | 0.55 |
| Total | 1100 | / |

Process Steps:

1) A lacosamide drug substance was sieved via a 30-mesh sieve to remove lumps to give the sieved lacosamide drug substance.

2) Sodium alginate, the sieved lacosamide drug substance obtained in step 1, crospovidone, polyoxyethylene, and colloidal silica were placed into a mixing tank for mixing for about 20 min to give a premix.

3) The premix obtained in step 2 was sized via a granulator with the pore size of the sieve being 2.0 mm and the sizing speed being 200 rpm. Then internal magnesium stearate was added thereto, the mixture was successively mixed for about 5 min, and dry granulation was performed to give a granule. The pinch roller pressure of the dry granulation was about 0-20 kg/cm', the pinch roller rotation speed was 8 HZ, the feeding speed was 2 HZ, the sizing rotation speed was 12 HZ, and the pore size of the selected secondary sizing sieve was 0.8 mm.

4) The amount of the external materials was converted, external anhydrous dicalcium phosphate was added to the granule obtained in step 3, and the mixture was successively mixed for about 15 min. Then external magnesium stearate was added, and the mixture was successively mixed for about 5 min. The final mixed material was compressed into a tablet (22.0 mm×10.9 mm almond-shaped shallow-arc stamp die).

The in vitro release of lacosamide was measured using USP (dissolution apparatus method 2,900 mL, an acetate buffer with a pH of 4.5, 50 rpm), and the in vitro release results are as follows:

| Time (min) | Cumulative release rate (%) |
|---|---|
| 0 | 0 |
| 30 | 4.5 |
| 60 | 7.5 |
| 120 | 12.7 |
| 240 | 21.4 |
| 360 | 29.6 |
| 540 | 41.3 |
| 720 | 52.6 |
| 960 | 66.0 |
| 1200 | 77.5 |
| 1440 | 87.2 |

The tablet dimension after dissolution and the results of rigidity and elasticity tests are as follows:

| dimension (mm × mm × mm) 24 h after dissolution | Rigidity (gf) | Elasticity |
|---|---|---|
| 37.30 * 21.82 * 19.71 | 522.6 | 0.715 |

Example 5

Matrix tablets containing the following components were produced according to the following procedures, in a batch of about 330 g.

| Component | Weight (mg) | Percentage (%) |
|---|---|---|
| Lacosamide | 200 | 18.18 |
| Sodium alginate | 280 | 25.45 |
| Crospovidone (Kollidon CL, BASF) | 180 | 16.36 |
| Colloidal silica | 6 | 0.55 |
| Magnesium stearate (internal) | 6 | 0.55 |
| Hydroxypropyl methylcellulose (K 15M, Ashland) (external) | 100 | 9.09 |
| Polyvinyl acetate povidone mixture (KSR, external) | 202 | 18.36 |
| Dicalcium phosphate dihydrate (external) | 120 | 10.91 |
| Magnesium stearate (external) | 6 | 0.55 |
| Total | 1100 | / |

Process Steps:

1) A lacosamide drug substance was sieved via a 30-mesh sieve to remove lumps to give the sieved lacosamide drug substance.

2) Sodium alginate, the sieved lacosamide drug substance obtained in step 1, crospovidone, and colloidal silica were placed into a mixing tank for mixing for about 20 min to give a premix.

3) The premix obtained in step 2 was sized via a granulator with the pore size of the sieve being 2.0 mm and the sizing speed being 200 rpm. Then internal magnesium stearate was added thereto, the mixture was successively mixed for about 5 min, and dry granulation was performed to give a granule. The pinch roller pressure of the dry granulation was about 0-20 kg/cm', the pinch roller rotation speed was 8 HZ, the feeding speed was 2 HZ, the sizing rotation speed was 12 HZ, and the pore size of the selected secondary sizing sieve was 0.8 mm.

4) The amount of the external materials was converted, external hydroxypropyl methylcellulose, a polyvinyl acetate povidone mixture, and dicalcium phosphate dihydrate were added to the granule obtained in step 3, and the mixture was successively mixed for about 15 min. Then external magnesium stearate was added, and the mixture was successively mixed for about 5 min. The final mixed material was compressed into a tablet (22.0 mm×10.9 mm almond-shaped shallow-arc stamp die).

The in vitro release of lacosamide was measured using USP (dissolution apparatus method 2,900 mL, 0.1N hydrochloric acid and an acetate buffer with a pH of 4.5, 50 rpm), and the in vitro release results are as follows:

| | Cumulative release rate (%) Dissolution medium | |
|---|---|---|
| Time (min) | 0.1N hydrochloric acid | acetate buffer with a pH of 4.5 |
| 0 | 0.0 | 0.0 |
| 30 | 7.9 | 5.5 |
| 60 | 12.9 | 9.1 |
| 120 | 20.1 | 15.1 |
| 240 | 30.0 | 25.5 |
| 360 | 37.7 | 35.7 |

-continued

| | Cumulative release rate (%) Dissolution medium | |
|---|---|---|
| Time (min) | 0.1N hydrochloric acid | acetate buffer with a pH of 4.5 |
| 540 | 46.5 | 50.0 |
| 720 | 54.4 | 64.5 |
| 960 | 63.0 | 80.1 |
| 1200 | 70.4 | 88.7 |
| 1440 | 77.6 | 92.9 |

The tablet dimension after dissolution and the results of rigidity and elasticity tests are as follows:

| Tablet dimension (mm × mm × mm) | Dissolution medium 0.1 N hydrochloric acid | |
|---|---|---|
| 24 h after dissolution | Rigidity (gf) | Elasticity |
| 27.76 * 14.43 * 11.13 | 309.3 | 0.623 |

| Tablet dimension (mm × mm × mm) | Dissolution medium acetate buffer with a pH of 4.5 | |
|---|---|---|
| 24 h after dissolution | Rigidity (gf) | Elasticity |
| 33.61 * 22.18 * 18.23 | 399.9 | 0.692 |

Example 6

Matrix tablets containing the following components were produced according to the following procedures, in a batch of about 300 g.

| Component | Weight (mg) | Percentage (%) |
|---|---|---|
| Lacosamide | 200 | 20.00 |
| Polyvinyl acetate povidone mixture (KSR) | 248 | 24.80 |
| Crospovidone (Kollidon CL, BASF) | 200 | 20.00 |
| Magnesium stearate (internal) | 6 | 0.60 |
| Sorbitol (external) | 150 | 15.00 |
| Sodium alginate (external) | 50 | 5.00 |
| Carbomer (971 PNF, Lubrizol) (external) | 60 | 6.00 |
| Hydroxypropyl methylcellulose (K 4M, Ashland) (external) | 80 | 8.00 |
| Magnesium stearate (external) | 6 | 0.60 |
| Total | 1000 | / |

Process Steps:

1) A lacosamide drug substance was sieved via a 30-mesh sieve to remove lumps to give the sieved lacosamide drug substance.

2) A polyvinyl acetate povidone mixture, the sieved lacosamide drug substance obtained in step 1, and crospovidone were placed into a mixing tank for mixing for about 20 min to give a premix.

3) The premix obtained in step 2 was sized via a granulator with the pore size of the sieve being 2.0 mm and the sizing speed being 200 rpm. Internal magnesium stearate was added thereto, the mixture was successively mixed for about 5 min, and dry granulation was performed to give a granule. The pinch roller pressure of the dry granulation was about 0-20 kg/cm', the pinch roller rotation speed was 8 HZ, the feeding speed was 3 HZ, the sizing rotation speed was 12 HZ, and the pore size of the selected secondary sizing sieve was 0.8 mm.

4) The amount of the external materials was converted, external sorbitol, carbomer, hydroxypropyl methylcellulose, and sodium alginate were added to the granule obtained in step 3, and the mixture was successively mixed for about 15 min. Then external magnesium stearate was added, and the mixture was successively mixed for about 5 min. The final mixed material was compressed into a tablet (22.0 mm×10.9 mm almond-shaped shallow-arc stamp die).

The in vitro release of lacosamide was measured using USP (dissolution apparatus method 2,900 mL, 0.1N hydrochloric acid and an acetate buffer with a pH of 4.5, 50 rpm), and the in vitro release results are as follows:

| Time (min) | Cumulative release rate (%) Dissolution medium | |
| | 0.1N hydrochloric acid | acetate buffer with a pH of 4.5 |
| --- | --- | --- |
| 0 | 0.0 | 0.0 |
| 30 | 8.3 | 5.5 |
| 60 | 13.1 | 9.2 |
| 120 | 20.3 | 15.5 |
| 240 | 29.4 | 26.1 |
| 360 | 37.4 | 35.8 |
| 540 | 45.8 | 49.8 |
| 720 | 52.7 | 63.8 |
| 960 | 60.8 | 79.8 |
| 1200 | 66.6 | 89.4 |
| 1440 | 71.6 | 94.7 |

The tablet dimension after dissolution and the results of rigidity and elasticity tests are as follows:

| Tablet dimension (mm × mm × mm) | Dissolution medium 0.1N hydrochloric acid | |
| 24 h after dissolution | Rigidity (gf) | Elasticity |
| --- | --- | --- |
| 24.71 * 13.45 * 10.02 | 650.0 | 0.791 |

| Tablet dimension (mm × mm × mm) | Dissolution medium acetate buffer with a pH of 4.5 | |
| 24 h after dissolution | Rigidity (gf) | Elasticity |
| --- | --- | --- |
| 38.40 * 18.97 * 12.79 | 54.4 | 0.737 |

Example 7

The component content was the same as in Example 5, and the production was performed in an expanded batch of 11000 g.
Process Steps:
1) A lacosamide drug substance was sieved via a 30-mesh sieve to remove lumps to give the sieved lacosamide drug substance.
2) Sodium alginate, the sieved lacosamide drug substance obtained in step 1, crospovidone, and colloidal silica were placed into a mixing tank for mixing for about 15 min to give a premix.
3) The premix obtained in step 2 was sized via a granulator with the pore size of the sieve being 2.0 mm and the sizing speed being 200 rpm. The premix was successively mixed for 5 min after sizing. Then internal magnesium stearate was added thereto, the mixture was successively mixed for about 5 min, and dry granulation was performed to give a granule. The pinch roller pressure of the dry granulation was about 2-5 bar, the lateral pressure was 2-5 bar, the pinch roller rotation speed was 5-15 rpm, the feeding speed was 5-15 rpm, the sizing rotation speed was 176 rpm, and the pore size of the selected secondary sizing sieve was 1.0 mm.
4) The amount of the external materials was converted, external hydroxypropylcellulose, a polyvinyl acetate povidone mixture, and dicalcium phosphate dihydrate were added to the granule obtained in step 3, and the mixture was successively mixed for about 15 min. The amount of external magnesium stearate was converted, the external magnesium stearate was then added, and the mixture was successively mixed for about 5 min. The final mixed material was compressed into a tablet (22.0 mm×10.9 mm almond-shaped shallow-arc stamp die).

The in vitro release of lacosamide was measured using USP (dissolution apparatus method 2,900 mL, 0.1N hydrochloric acid and an acetate buffer with a pH of 4.5, 50 rpm), and the in vitro release results are as follows:

| Time (min) | Cumulative release rate (%) Dissolution medium | |
| | 0.1N hydrochloric acid | acetate buffer with a pH of 4.5 |
| --- | --- | --- |
| 0 | 0.0 | 0.0 |
| 30 | 6.5 | 4.9 |
| 60 | 10.9 | 8.6 |
| 120 | 17.3 | 14.3 |
| 240 | 26.2 | 24.1 |
| 360 | 33.8 | 34.0 |
| 540 | 41.9 | 46.8 |
| 720 | 49.1 | 60.5 |
| 960 | 56.5 | 77.7 |
| 1200 | 63.2 | 90.6 |
| 1440 | 68.9 | 97.6 |

Example 8

A comparative study of a pharmacokinetic evaluation test of the homemade lacosamide pharmaceutical composition obtained in Example 7 and the lacosamide tablet in Reference Example 1 orally administered in beagle dogs was conducted in the present disclosure.

In the experiment, 6 beagle dogs were used and divided into 2 groups (3 dogs/sex for each group). One tablet of the test formulation (200 mg/tablet, single administration) and 2 tablets of the control formulation (100 mg/tablet, single administration) were orally administered to group 1 and group 2 in the first cycle, respectively. After a washout period of at least one week as an interval, 2 tablets of the control formulation (100 mg/tablet, one tablet at a time, with an interval of 8 h) and 1 tablet of the test formulation (200 mg/tablet, single administration) were orally administered to group 1 and group 2 in the second cycle, respectively.

Sampling time points for group 1 in the first cycle were 0.5 h, 1 h, 2 h, 3 h, 4 h, 5 h, 6 h, 8 h, 12 h, 16 h, 24 h, 36 h, and 48 h after administration, 13 time points in total; sampling time points for group 2 in the first cycle were 0.25 h, 0.5 h, 1 h, 1.5 h, 2 h, 2.5 h, 3 h, 4 h, 6 h, 8 h, 12 h, 24 h, and 48 h after administration, 13 time points in total.

Sampling time points for group 1 in the second cycle were 0.25 h, 0.5 h, 1 h, 1.5 h, 2 h, 2.5 h, 3 h, 5 h, 8 h (after the 8-h blood collection, the second administration was performed), 8.25 h, 8.5 h, 9 h, 9.5 h, 10 h, 10.5 h, 11 h, 13 h, 16 h, 24 h, and 48 h after administration, 20 time points in total; sampling time points for group 2 in the second cycle were 0.5 h, 1 h, 2 h, 3 h, 4 h, 5 h, 6 h, 8 h, 12 h, 16 h, 24 h, 36 h, and 48 h after administration, 13 time points in total.

According to the time points set, approximately 500 uL of whole blood was collected from the cephalic vein of fore-limb or other suitable veins into an anticoagulation centri-fuge tube containing K2-EDTA, and the tube was stored on wet ice prior to centrifugation. The plasma was obtained by centrifuging the sample within 2 h after sampling (at 2-8° C. for 5 min at 3000 g centrifugal force). The plasma sample was first stored frozen in dry ice temporarily, and then placed in a refrigerator at −60° C. for long-time storage until sample analysis.

After the plasma sample was collected, the concentration of lacosamide in the plasma of the beagle dog was quanti-tatively determined by adopting a verified liquid chroma-tography-mass spectrometer (LC-MS/MS) analysis method. Pharmacokinetic parameters were calculated in a non-com-partmental model via WinNonlin 8.2 software.

A paired two-tailed T-test was performed to test the pharmacokinetic parameters $T_{max}$, $C_{max}$, $AUC_{last}$, $AUC_{INF}$, $T_{1/2}$, and $MRT_{INF}$ using Microsoft Excel 2007. The test results show that:

After 1 tablet of the BCM-332 test formulation (200 mg/tablet, single administration) and 2 tablets of the control formulation (100 mg/tablet, one tablet at a time, with an interval of 8 h) were orally administered to the male beagle dog, $T_{max}$, $AUC_{last}$, $AUC_{INF}$, and $T_{1/2}$ were not significantly different (P>0.05), and $C_{max}$ and $MRT_{INF}$ were statistically different (P<0.05).

After 1 tablet of the BCM-332 test formulation (200 mg/tablet, single administration) and 2 tablets of the control formulation (100 mg/tablet, single administration) were orally administered to the female beagle dog, $T_{max}$, $AUC_{last}$, $AUC_{INF}$, and $T_{1/2}$ were not significantly different (P>0.05), $C_{max}$ was statistically different (P<0.05), and $MRT_{INF}$ was significantly statistically different (P<0.01).

Figure 3:
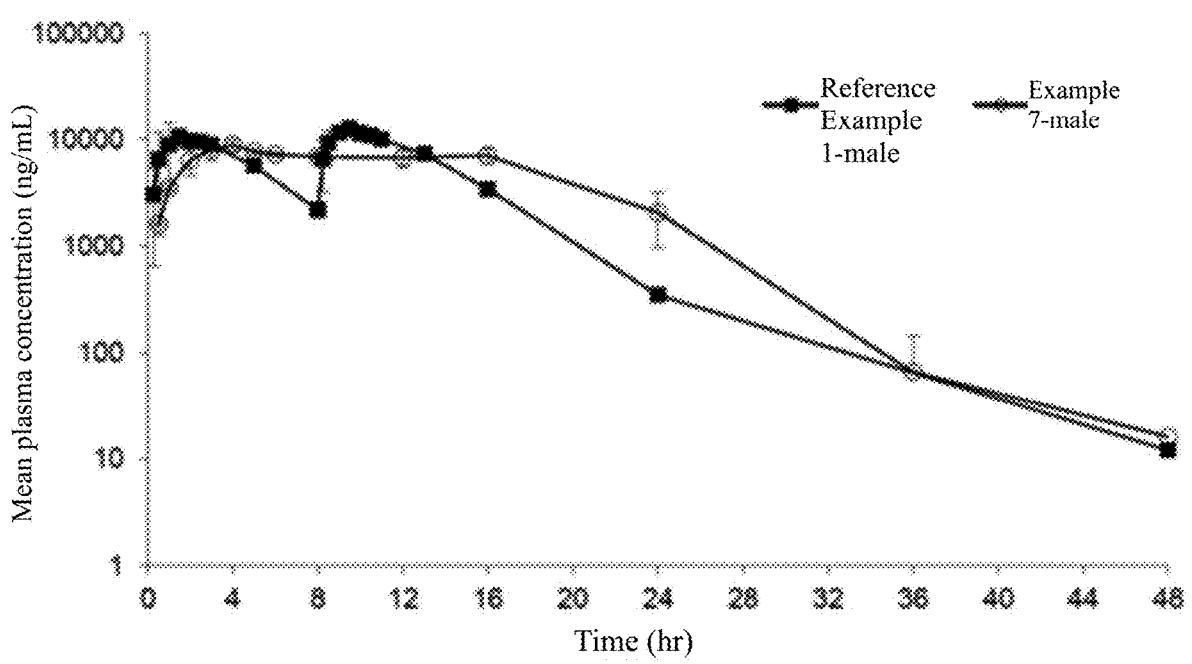
FIG. 3 is a graph of the mean drug concentration-time curves of lacosamide after oral administration of the formulations in Example 7 and Reference Example 1 to male beagle dogs in Example 8 (N=3).
Figure 4:
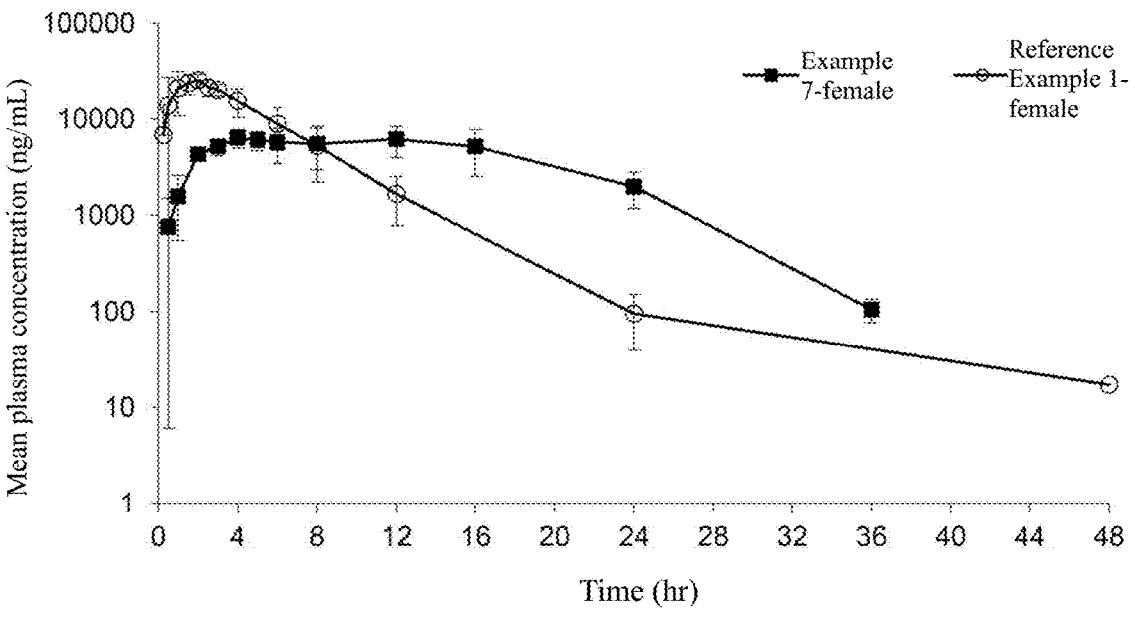
FIG. 4 is a graph of the mean drug concentration-time curves of lacosamide after oral administration of the formulations in Example 7 and Reference Example 1 to female beagle dogs in Example 8 (N=3).

The dissolution curves of Examples 2 and 5-7 in 0.1N hydrochloric acid are shown in FIG. 1; the dissolution curves of Examples 1-7 in an acetate buffer with a pH of 4.5 are shown in FIG. 2; the results of the pharmacokinetic evaluation test for oral administration of the beagle dogs described in Example 8 are shown in Tables 1 and 2; the plasma concentration-time curves of the pharmacokinetic evaluation test for oral administration of the beagle dogs described in Example 8 are shown in FIGS. 3 and 4; the T-test results of the pharmacokinetic parameters of the pharmacokinetic evaluation test for oral administration of the beagle dogs described in Example 8 are shown in Tables 3 and 4.

TABLE 1

Mean pharmacokinetic parameters of lacosamide after oral administration of formulations in Example 7 and Reference Example 1 to male beagle dogs (Mean ± SD, N = 3)

| PK Parameters | Example 7 (first cycle) (one tablet for single administration) | Reference Example 1 (second cycle) (administration twice, one tablet at a time, with an interval of 8 h) |
|---|---|---|
| $T_{max}$ (hr) | 8.00 ± 6.93 | 9.33 ± 0.289 |
| $C_{max}$ (ng/ml) | 9175 ± 1332 | 12757 ± 1545 |
| $T_{1/2}$ (hr) | 3.52 ± 0.00114 | 2.86 ± 0.744 |
| $AUC_{last}$ (hr * ng/ml) | 156158 ± 30937 | 132250 ± 13947 |
| $AUC_{INF}$ (hr * ng/mL) | 149802 ± 40353 | 133024 ± 13334 |
| $MRT_{INF}$ (hr) | 11.9 ± 1.05 | 9.10 ± 0.113 |

TABLE 2

Mean pharmacokinetic parameters of lacosamide after oral administration of formulations in Example 7 and Reference Example 1 to female beagle dogs (Mean ± SD, N = 3)

| PK Parameters | Example 7 (second cycle) (one tablet for single administration) | Reference Example 1 (first cycle) (two tablets for single administration) |
|---|---|---|
| $T_{max}$ (hr) | 9.33 ± 4.62 | 1.67 ± 0577 |
| $C_{max}$ (ng/ml) | 7092 ± 464 | 25936 ± 4939 |
| $T_{1/2}$ (hr) | 3.38 ± 0.986 | 3.26 ± 0.817 |
| $AUC_{last}$ (hr * ng/ml) | 125017 ± 8936 | 138495 ± 50607 |
| $AUC_{INF}$ (hr * ng/mL) | 125606 ± 9299 | 138819 ± 50875 |
| $MRT_{INF}$ (hr) | 12.6 ± 0.745 | 4.56 ± 0.286 |

TABLE 3

T-test results of pharmacokinetic parameters after oral administration of formulations in Example 7 and Reference Example 1 to male beagle dogs

| PK parameters (Unit) | T-Test |
|---|---|
| $T_{max}$ (hr) | 0.779 |
| $C_{max}$ (ng/ml) | 0.014* |
| $T_{1/2}$ (hr) | 0.605 |
| $AUC_{last}$ (hr * ng/ml) | 0.255 |
| $AUC_{INF}$ (hr * ng/mL) | 0.615 |
| $MRT_{INF}$ (hr) | 0.035* |

*p < 0.05, **p < 0.01 (two tailed T-test)

TABLE 4

T-test results of pharmacokinetic parameters after oral administration of formulations in Example 7 and Reference Example 1 to female beagle dogs

| PK parameters (Unit) | T-Test |
|---|---|
| $T_{max}$ (hr) | 0.115 |
| $C_{max}$ (ng/ml) | 0.021* |
| $T_{1/2}$ (hr) | 0.838 |
| $AUC_{last}$ (hr * ng/ml) | 0.632 |
| $AUC_{INF}$ (hr * ng/mL) | 0.639 |
| $MRT_{INF}$ (hr) | 0.001** |

*p < 0.05, **p < 0.01 (two tailed T-test)

The observations about the state of the beagle dogs during the test are as follows:

| Period of administration | Animal No. | Symptom |
|---|---|---|
| First cycle | #5-8612903 (dosed by Reference Example) | 1 h and 40 min after administration in the first cycle, the dog vomited a small amount of chyme with the muscle trembling and slightly twitching, and recovery was at 2.5 h |
| | #6-8621715 (dosed by Reference Example) | 1.5 h after administration in the first cycle, the dog lay in a cage in low energy with the whole body twitching. At 1 h and 44 min, the dog vomited a large amount of chyme. At 2 h, the dog squatted in the cage with the muscle of the whole body trembling and slightly twitching. At 2.5 h, a large amount of chyme vomit was observed. At 3 h, the dog was in low energy and had decreased activity. Recovery was at 4 h |
| | All beagle dogs dosed by | The dogs were free from the adverse effect described above and other |

-continued

| Period of administration | Animal No. | Symptom |
|---|---|---|
| | Example 7 | abnormal conditions during the whole process |

As can be seen from the test results of Examples 1-8, the lacosamide pharmaceutical composition of the present disclosure shows a good sustained-release effect in vitro and in vivo, can be rapidly expanded in the in vitro dissolution process, and has good rigidity and elasticity after expansion, which provides a stable and good gastro-retentive effect for the product. Furthermore, all beagle dogs dosed by Example 7 are free from abnormal conditions during the whole process, indicating that the composition of the present disclosure has better safety.

The invention claimed is:

1. A pharmaceutical composition, wherein the pharmaceutical composition is a 24-hour sustained-release gastro-retentive tablet comprising an active pharmaceutical ingredient, a skeleton material, a swelling material and a disintegrant, wherein the active pharmaceutical ingredient is lacosamide or a pharmaceutically acceptable salt of lacosamide, and the weight percentage of the active pharmaceutical ingredient is 5.0%-40.0%, the skeleton material is selected from one or more of a polyvinyl acetate povidone mixture, sodium alginate, and hydroxypropyl methylcellulose, when the skeleton material is the polyvinyl acetate povidone mixture, the polyvinyl acetate povidone mixture comprises polyvinyl acetate povidone (PVAc) and polyvinylpyrrolidone (PVP) in a weight ratio of 80:19 and has a weight percentage of 18.36%-24.68%, when the skeleton material is the sodium alginate, the skeleton material has a weight percentage of 5%-35.09%, when the skeleton material is the hydroxypropyl methylcellulose, the skeleton material has a weight percentage of 8%-17.27%;

the swelling material is selected from one or two of polyoxyethylene and carbomer, and the weight percentage of the swelling material is 1.0%-60.0%;

the disintegrant is selected from one or more of crospovidone, sodium carboxymethyl starch, croscarmellose sodium, carboxymethylcellulose calcium, and low-substituted hydroxypropylcellulose, and the weight percentage of the disintegrant is 5%-30.0%; and under the United States Pharmacopeia (USP) dissolution apparatus method 2 that uses 900 mL of 0.1N hydrochloric acid at 50 rpm, or uses 900 mL of an acetate buffer with a pH of 4.5 at 50 rpm, dissolution of the pharmaceutical composition simultaneously satisfies the following three criteria:

A) no more than 40% of the active pharmaceutical ingredient is dissolved within 1 hour;

B) 20%-70% of the active pharmaceutical ingredient is dissolved within 6 hours; and C) no less than 65% of the active pharmaceutical ingredient is dissolved within 24 hours.

2. The pharmaceutical composition of claim 1, wherein:

when the swelling material is polyoxyethylene, the swelling material has a weight percentage of 15%-20%;

when the swelling material is the carbomer, the swelling material has a weight percentage of 3%-6%; and under the USP method of dissolution apparatus method 2, dissolution of the pharmaceutical composition satisfies:

no more than 30% of the active pharmaceutical ingredient is dissolved within 1 hour;

30%-55% of the active pharmaceutical ingredient is dissolved within 6 hours; and no less than 80% of the active pharmaceutical ingredient is dissolved within 24 hours.

3. The pharmaceutical composition as claimed in claim 1, further comprising one or more components selected from a skeleton strength regulator, a diluent, and a lubricant, wherein the skeleton strength regulator is selected from dicalcium phosphate and dicalcium phosphate dihydrate;

the weight percentage of the skeleton regulator is 10%-15.0%;

the diluent is one or more selected from dextrose, lactose monohydrate, anhydrous lactose, sucrose, mannitol, xylitol, sorbitol, microcrystalline cellulose, starch, pregelatinized starch, dicalcium phosphate dihydrate, anhydrous dicalcium phosphate, and cyclodextrin or a derivative thereof; and the weight percentage of the diluent is 10%-40%;

the lubricant is one or more selected from talc, stearic acid, metal stearate, stearate ester, colloidal silica, glyceryl behenate, sodium lauryl sulfate, hydrogenated vegetable oil, mineral oil, poloxamer, polyethylene glycol, and sodium chloride; and the weight percentage of the lubricant is 0.5%-2.0%.

4. The pharmaceutical composition as claimed in claim 1, selected from formula one, formula two, formula three, formula four, formula five, and formula six, wherein:

the formula one comprises: 18.18% lacosamide, 35.09% sodium alginate, 13.64% crospovidone, 11.73% anhydrous dicalcium phosphate, 1.10% magnesium stearate, 3.00% carbomer, and 17.27% hydroxypropyl methylcellulose;

the formula two comprises: 20.00% lacosamide, 24.80% polyvinyl acetate povidone mixture, 20.00% crospovidone, 1.20% magnesium stearate, 20.00% sorbitol, 6.00% carbomer, and 8.00% hydroxypropyl methylcellulose;

the formula three comprises: 18.18% lacosamide, 35.09% sodium alginate, 16.64% crospovidone, 16.73% hydroxypropyl methylcellulose, 0.55% colloidal silica, 1.10% magnesium stearate, and 11.73% anhydrous dicalcium phosphate;

the formula four comprises: 18.18% lacosamide, 35.09% sodium alginate, 16.64% crospovidone, 16.73% polyoxyethylene, 0.55% colloidal silica, 1.10% magnesium stearate, and 11.73% anhydrous dicalcium phosphate;

the formula five comprises: 18.18% lacosamide, 25.45% sodium alginate, 16.36% crospovidone, 0.55% colloidal silica, 1.10% magnesium stearate, 9.09% hydroxypropyl methylcellulose, 18.36% polyvinyl acetate povidone mixture, and 10.91% dicalcium phosphate dihydrate; and the formula six comprises: 20.00% lacosamide, 24.80% polyvinyl acetate povidone mixture, 20.00% crospovidone, 1.20% magnesium stearate, 15.00% sorbitol, 5.00% sodium alginate, 6.00% carbomer, and 8.00% hydroxypropyl methylcellulose.

5. A preparation method for the pharmaceutical composition as claimed in claim 1, comprising a dry granulation process.

6. A method for treating and/or preventing acute and chronic pain, comprising administering the pharmaceutical composition as claimed in claim 1 to a subject in need thereof.

7. The method as claimed in claim 6, wherein the chronic pain is pain which extends over a period of 3-6 months or more, but before or after the period of time, one of the following characteristic signs is present, and a vegetative nervous dysfunction signs occur, lassitude, sleep disorders, decreased appetite, loss of taste, weight loss, hyposexuality, and constipation.

8. The pharmaceutical composition as claimed in claim 1, wherein the particle size of the active pharmaceutical ingredient is less than or equal to 30 mesh.

9. The pharmaceutical composition as claimed in claim 1, wherein the gastro-retentive tablet has a dosage ranging from 100 mg to 400 mg.

10. The method as claimed in claim 6, wherein the acute or chronic pain is non-neuropathic inflammatory pain.

11. The method as claimed in claim 6, wherein the acute or chronic pain is chronic inflammatory pain.

12. The method as claimed in claim 7, wherein the acute or chronic pain is rheumatoid arthritis pain or secondary osteoarthritis pain.

\*    \*    \*    \*    \*